United States Patent [19]

Saxena et al.

[11] Patent Number: 4,865,729
[45] Date of Patent: * Sep. 12, 1989

[54] RADIAL THIN LAYER CHROMATOGRAPHY

[75] Inventors: Vinit Saxena; Brian D. Andresen, both of Pleasanton, Calif.

[73] Assignee: Sepragen Corporation, San Leandro, Calif.

[*] Notice: The portion of the term of this patent subsequent to Dec. 9, 2003 has been disclaimed.

[21] Appl. No.: 199,469

[22] Filed: May 27, 1988

Related U.S. Application Data

[63] Continuation-in-part of Ser. No. 939,557, Dec. 9, 1986, abandoned, which is a continuation-in-part of Ser. No. 869,295, Jun. 2, 1986, Pat. No. 4,676,898, which is a continuation-in-part of Ser. No. 794,727, Nov. 4, 1985, Pat. No. 4,627,918.

[51] Int. Cl.$^4$ ............................................. B01D 15/08
[52] U.S. Cl. .............................. 210/198.2; 210/198.3; 210/658
[58] Field of Search ................ 210/658, 198.2, 198.3; 422/70; 436/162

[56] References Cited

U.S. PATENT DOCUMENTS

| | | | |
|---|---|---|---|
| 2,708,519 | 5/1955 | Novak | 210/198.2 |
| 2,986,280 | 5/1961 | Magnuson | 210/198.3 |
| 3,295,683 | 1/1967 | Litt | 210/658 |
| 3,413,842 | 12/1968 | Hecker | 210/658 |
| 3,477,950 | 11/1969 | Clement | 210/198.3 |
| 3,503,712 | 3/1970 | Sussman | 210/198.2 |
| 3,928,203 | 12/1975 | Kremer | 210/198.3 |
| 4,077,886 | 3/1978 | Fukuda | 210/198.2 |
| 4,346,001 | 8/1982 | Tyihak | 210/198.3 |
| 4,627,918 | 12/1986 | Saxena | 210/198.2 |
| 4,636,315 | 1/1987 | Allen | 210/198.2 |

FOREIGN PATENT DOCUMENTS

| 1262493 | 2/1972 | United Kingdom | 210/658 |
|---|---|---|---|
| 2166366 | 5/1986 | United Kingdom | 210/198.3 |

Primary Examiner—Ernest G. Therkorn
Attorney, Agent, or Firm—Shyamala T. Rajender

[57] ABSTRACT

An improved liquid chromatography column having a horizontal flow of the liquid through the separating medium utilizing an improved fluid distribution system is disclosed. The improved fluid distribution system includes a screen or mesh arrangement, and a thin layer, plate or wafer-like separation medium. The screen or mesh type distribution system enables uniform distribution of the sample or eluting fluid radially over 360° around the periphery of the separating medium bed, thus eliminating the high machining costs and other problems associated with systems employing grooves or passageways type distribution systems. The improved column as a whole may be fabricated so as to be disposable or may be constructed to have an even more simplified fluid distribution arrangement.

32 Claims, 4 Drawing Sheets

RADIAL THIN LAYER CHROMATOGRAPHY

RELATED APPLICATIONS

This is a continuation-in-part of application Ser. No. 939,557 filed Dec. 9, 1986, now abandoned, which is a continuation-in-part and an improvement over the invention described and claimed in application Ser. No. 869,295 filed June 2, 1986, now U.S. Pat. No. 4,676,898 issued June 30, 1987, which is a continuation-in-part of application Ser. No. 794,727 filed Nov. 4, 1985, now U.S. Pat. No. 4,627,918 issued Dec. 9, 1986 in the name of Vinit Saxena. The improvement described and claimed in this application is also an improvement over the chromatographic column described in applications Ser. No. 904,912 filed Sept. 8, 1986 and Ser. No. 906,846 filed Sept. 15, 1986, now U.S. Pat. No. 4,708,782 issued Nov. 24, 1987, in the names of Vinit Saxena and Brian D. Andresen.

This invention relates generally to chromatography systems, and more particularly to an improved thin layer chromatographic system which utilizes horizontal or radial flow through the separating medium, and a novel sample and eluant inlet and distribution arrangement for horizontal flow chromatographic columns.

BACKGROUND OF THE INVENTION

Chromatography, as it is generally used, is a technique for the separation of various components of a "sample mixture". In a liquid chromatography system, a sample followed by an elution fluid is injected into a chromatographic separation column. The separation column contains a packing or matrix medium or material which interacts with the various components of the sample fluid to be separated. The composition of the separating medium depends on the fluid being directed therethrough to effect the desired separation. As the sample and elution fluids pass through the separating matrix or medium, the various components of the sample fluid travel at different rates through the separating medium or matrix as a result of differential interactions with the separating medium or matrix. Consequently, these components emerge separated (different elution times and different $R_f$ values) in the outlet or effluent from the separation medium or matrix, as is well known in the art.

Thin layer chromatography, is one of the chromatographic techniques developed from paper chromatography, and is widely used for separating the different components in a complex mixture. The technique, generally, comprises the transfer of a sample material to be analyzed to a spot or spots on the chromatographic plate or sheet, drying the deposited sample, and initiating the differential migration of the various components of the sample material by flowing appropriate solvent or solvents across the surface of the plate, in vertical, horizontal, circular or anticircular modes. In the vertical mode, the solvent travels up or down the plate or sheet. In the horizontal mode, the solvent travels from one side to the other side of the plate or sheet. In the circular mode, the solvent travels from the center outward in all directions and in the anticircular flow thin layer chromatography, the solvent travels from the periphery to the center of the sorption layer.

Various types of the vertical flow separation columns and other thin layer chromatographic techniques are known in the art and are exemplified by the following patents.

U.S. Pat. No. 4,388,193 issued June 14, 1983 to Paul Buncak discloses a thin layer chromatographic method where a pressurized, developing solvent is conducted from a dosing container directly on to the sorption layer through an exit opening and thence to a surface slit.

U.S. Pat. No. 4,351,800 issued Sept. 28, 1982 to R. H. Kopp et al., describes an apparatus for the application of multiple samples to thin layer chromatographic plates.

U.S. Pat. No. 4,346,001, issued Aug. 24, 1982 to E. Tyihak et al., discloses an over-pressurized thin layer chromatographic apparatus where the sorption layer vs covered by a membrane which is filled and externally pressurized by a fluid medium. A transparent cover plate provided with sealed inlets is fitted over the membrane and serves to introduce sample and solvent to the sorption layer through the membrane.

U.S. Pat. No. 3,928,203 issued Dec. 23, 1975 to R. D. Kremer is directed to a thin layer chromatography apparatus which includes a sorption layer on which a plurality of sample spots may be positioned. A base plate providing a plurality of solvent wells and a wick holding plate for transferring the solvent from the solvent wells to the sorption layer are employed.

U.S. Pat. No. 4,469,601 issued Sept. 4, 1984 to L. A. Beaver et al., describes a system and apparatus for multi-dimensional real-time chromatography.

U.S. Pat. No. 4,604,198 issued Aug. 5, 1986 to N. Dailey et al., discloses a multicartridge chromatography housing.

In all these prior techniques, the eluted sample patterns need to be separately developed or eluted off the plate or sheet for further analysis. The thin layer chromatographic (TLC) systems described in the above described patents, are designed to speed up and enhance analysis of the compounds have to be separated. In all these methods, detection of the separated constituents is done by means of traditional TLC methods such as staining, scanning the TLC plate surface and the like. These prior art methods, therefore, do not readily lend themselves to operation in the High Performance Liquid Chromatography (HPLC) mode or for handling at one time or in a continuous fashion, large quantities of sample material to be separated.

A horizontal flow chromatography system is described in U.S. Pat. No. 4,627,918 reference to which was made earlier.

With the need for high performance chromatography, horizontal flow type chromatographic columns were developed. Such horizontal or radial flow columns are described and claimed in the earlier referenced U.S. Pat. Nos. 4,627,918 and 4,676,898. In the horizontal or radial flow type columns, the sample and elution fluids are introduced via a distributor to the outer periphery or circumferential wall or surface of the separating medium or matrix, and the fluids pass horizontally or radially inwardly through the separation medium to a central or collection port and then elute from the column at different times and at different rates.

Various types of horizontal flow type columns have been recently developed. Such columns include those of a disposable type or of the type which utilize a disposable medium. Copending applications Ser. No. 869,295, now U.S. Pat. No. 4,676,898 issued June 30, 1987, Ser. No. 904,912, now U.S. Pat. No. 4,740,298 issued Apr. 26, 1988, and Ser. No. 906,646, now U.S. Pat. No. 4,708,782, issued Nov. 24, 1987 referenced herein earlier, disclose and claim liquid chromatographic column which utilize a disposable type separation medium or matrix. Copending applications Ser. No. 904,912, now U.S. Pat. No. 4,740,298 issued Apr. 26, 1988, and Ser. No. 906,646, now U.S. Pat. No. 4,708,782, issued Nov. 24, 1987 also describe and claim a "wafer" of or a thin matrix-supported separation medium. While the horizontal or radial flow type columns described therein enable the handling of high flow rates at relatively low operational pressures without sacrificing the desired high resolution, there still exists a need for more simplified separation and/or fluid distribution systems which provide high resolution, and for methods and means for producing them less expensively.

Accordingly, it is an object or this invention to provide an improved horizontal or radial flow chromatography column.

A further object is to provide an improved thin layer chromatography system utilizing radial or horizontal flow.

Another object of the invention is to provide a liquid chromatography column with an improved fluid distribution system.

Still another object of the invention is to provide a simplified but sturdy fluid inlet distribution arrangement for thin layer or thin matrix type chromatography systems which utilize horizontal or radial flow.

Yet another object of the invention is to provide a less expensive horizontal flow chromatography column or system which utilizes an improved fluid system and a "wafer" type separation medium or matrix.

A further object is to provide for a means of continuous removal and on line detection of the separated constituents from the chromatography column.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to an improved horizontal or radial flow, thin layer chromatography system. The improved column of this invention utilizes a simplified and more economically fabricated liquid inlet distribution and flow arrangement. In addition, one disclosed embodiment utilizes a "wafer" or a thin layer or a thin, matrix or substrate supported layer of the separation medium, which serves to reduce the size and cost of liquid chromatographic columns, without sacrificing the desired high flow rates, high resolution and sturdy construction. Thus the invention provides a simplified, sturdy and integrally fabricated chromatography column which may be totally disposable as a unit or which provides for the rapid replacement of the separation medium, which may be composed of a "wafer" or thin plate, substrate supported or matrix supported type separation medium.

More specifically, the improved chromatographic column or system of this invention includes a sample and elution fluid inlet and distribution system or arrangement which eliminates the radially extending grooves, channels or passageways in the upper end section or cap which extend from a centrally located opening to the outer periphery of the separating medium, as illustrated and described in each of the copending applications and issued patents referenced herein earlier. By eliminating the grooves, channels or passageways, a great deal of machining requirements, the cost of production and other problems associated therewith at the required analytical or diminutive level, are significantly reduced.

The improved fluid distribution system or arrangement basically comprises a screen or mesh positioned in a countersunk section of the end cap and retained therein by a member having a diameter slightly smaller than the periphery of the countersunk section of the end cap to form an annular opening, which allows for the passage of the fluid therebetween over essentially the entire circumference of the retainer member. The retainer member is maintained in a centered or floating position by a plurality of balls, shims, or thin supports positioned in spaced relation around the periphery thereof. Thus, the inlet sample and elution fluids are directed through a central opening in the end cap and onto the screen or mesh, whereafter the fluid is directed radially outward through the screen or mesh over a 360° angle area and passes through the annular opening to the outer area of the separation medium, which in certain of the illustrated embodiments, is in the form of a "wafer" or a thin support layer. The fluid then passes radially or horizontally inwardly through the separation medium, with the "wafer" or thin layer of the separation medium being supported on a suitable matrix or substrate, such as a glass, quartz or ceramic plate, filter paper, polymer sheet or membrane such as polyester, polyacetate and the like, a porous substrate, paper and the like. The separation medium may be any suitable separation material known in the art, and includes, without limitation, cellulose, agarose, or derivatives thereof, anionic and cationic exchange resins, polymer beads, glass, quartz or ceramic beads and the like. The separation medium may be coated, deposited or otherwise secured on or to the support member or layer or matrix by any suitable method as is known in the art. As used herein, the term "deposited" or "secured" is intended to include any and all means of depositing, coating or securing the separation medium to the support or matrix member. In one embodiment, the separation medium is in the form of small beads retained within a small chamber.

The separated components or constituents of the sample fluid are then directed into a centrally located collection port, whereafter they exit from the column to a point of use. The fluid components may be directed to the point of use, such as a fraction collector or a mass spectrometer by means such as a moving belt or to an electrophoresis apparatus or system as described and claimed in copending applications or issued patents referred to herein earlier.

The present invention exhibits several advantages over prior art devices. The system involves solvent flow-through on a continuous basis, so that laborious preparations normally involved in TLC are eliminated. On-line, real-time detection using various techniques such as, for example, ultra violet absorption, colorimetric, amperometric, radiometric measurements, conductance, electrochemical techniques and the like, which was not possible with the earlier TLC methodologies.

Because of the on-line detection, analysis is speeded up several fold. Gradient separations are made possible on a continuous basis by varying the solvent composition with time. Continuously eluting fractions can be collected easily for further analysis, if desired. Furthermore, TLC plates, which are far less expensive than HPLC columns, can now be used for analysis with the same ease and versatility as the more expensive and cumbersome HPLC columns.

DETAILED DESCRIPTION OF THE INVENTION

The present invention is directed to an improved thin layer chromatographic system which utilizes radial flow and an improved fluid distribution and flow system therefor. The improved fluid distribution system may also be used with other types of chromatographic apparatus and systems, especially those based on horizontal or radial flow of the sample and carrier or eluant material. As used herein, the terms "horizontal" or "radial" flow or mode are defined as the flow of the sample and/or carrier or eluant fluid through the separation medium of the chromatographic system or column in a direction that is substantially perpendicular to the vertical or longitudinal axis of the column or system. The terms are used interchangeably to denote the mode of flow of the sample or eluant fluid through the separation medium. Similarly, the terms "chromatography or chromatographic system" includes, without limitation, any type of a column or column members which retain a separation medium therein or therebetween or sandwich-type vertical or horizontal plates or retainer members between which the separation medium is retained in the form of a thin bed or a wafer, or a thin layer of separation material coated or deposited on a thin plate, sheet or on any suitable support matrix or substrate.

The improved chromatographic system or column of this invention provides a fluid inlet and radial distribution system which eliminates grooved or channelled arrangement of previously described horizontal flow-type columns or systems for fluid distribution, but still retains the 360° fluid distribution to the outer area or periphery of the separation medium. In certain of the illustrated embodiments, the improved column or system also utilizes a disposable "wafer", "plate" or thin matrix-supported type separation medium. The column of this invention may also be constructed as an integral unit so as to be disposable or fabricated for ready dismantling and interchanging the separation medium wafer or plate which may be fabricated to be disposable. The screen or mesh of the improved fluid distribution system of the embodiment illustrated in FIG. 1, enables a 360° distribution of the sample, carrier and eluant fluids so as to provide uniform distribution thereof to the outer surface areas or periphery of the separation medium. The screen or mesh arrangement is eliminated in the embodiment of FIG. 3. This embodiment is particularly applicable where elution flow under a relatively higher pressure is desirable.

Figure 1:
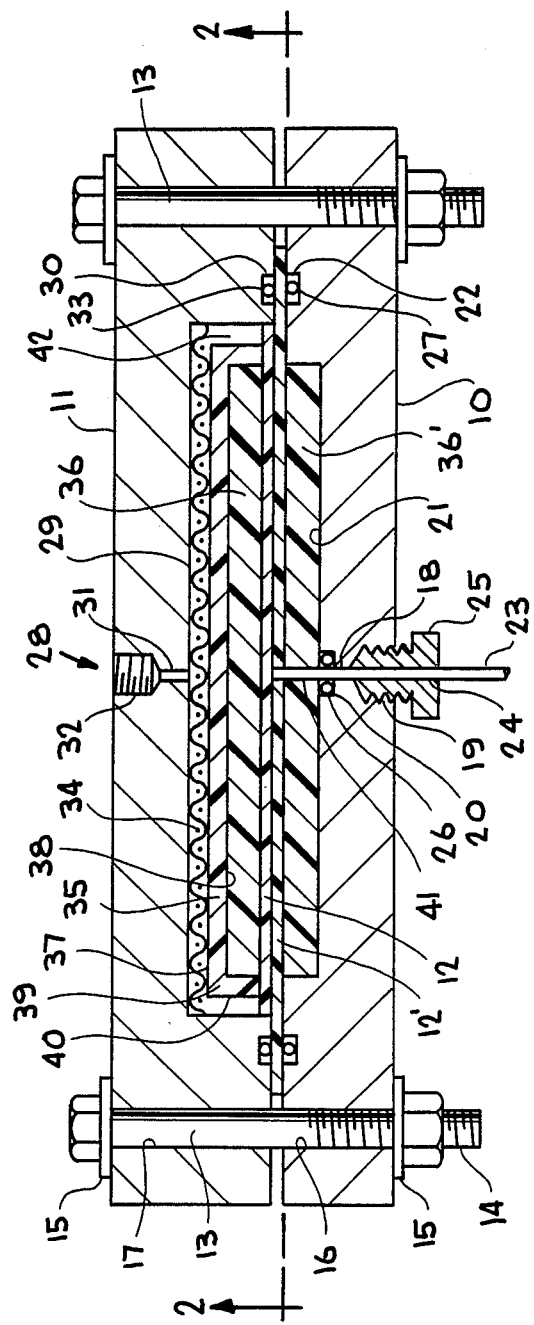
FIG. 1 is a cross-sectional view of an embodiment of the improved chromatographic system in accordance with the invention and which utilizes a "wafer" type separation medium.
Figure 2:
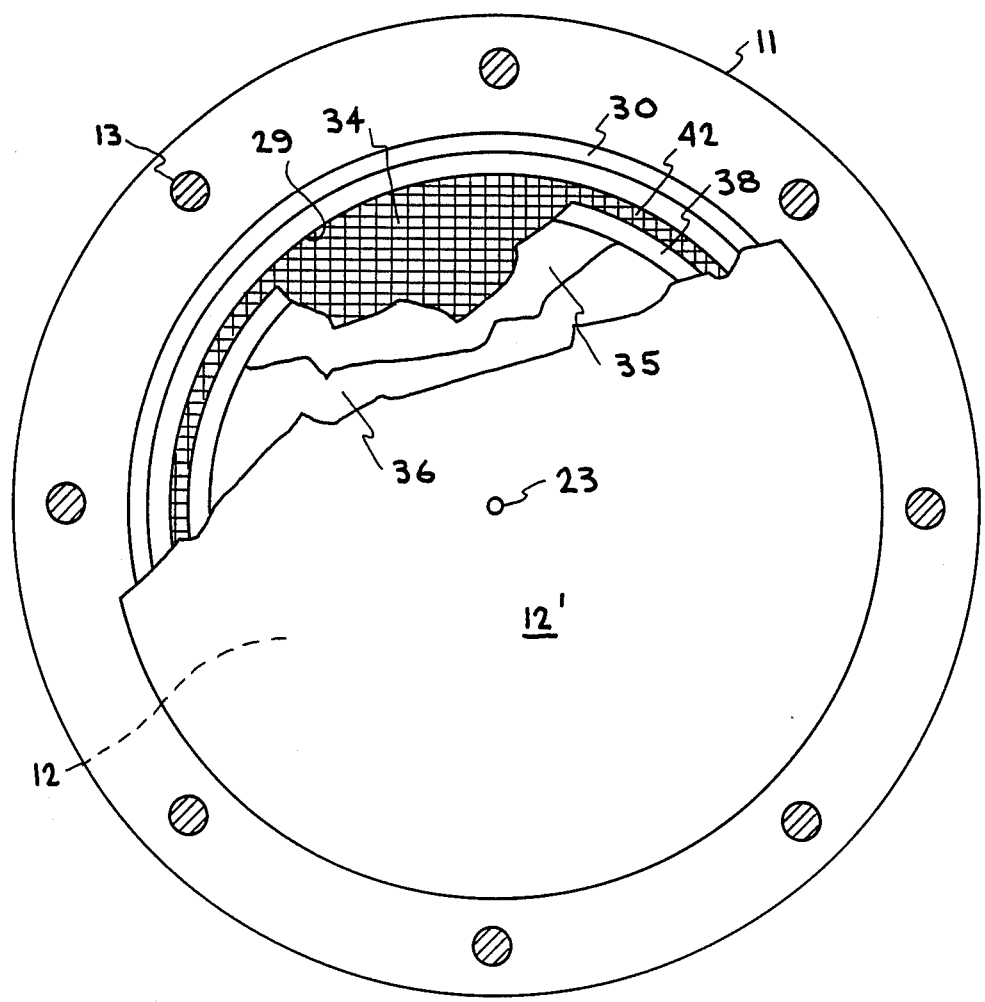
FIG. 2 is an end view of the upper section or end cap of FIG. 1, with a section of the retainer member of the fluid distribution system cut away to illustrate more clearly the screen or mesh used for the even or uniform radial distribution of the sample and/or eluting fluid.

Referring now to the drawings, the embodiments of the improved chromatography column or system illustrated in FIGS. 1 and 2, comprises basically a housing formed by a lower section or end cap or plate 10 and an upper section or end cap or plate 11 and within which a "wafer" or a thin "plate" or layer or matrix of a separation medium 12 secured to a non-permeable support member or layer 12', is retained between end caps or plates 10 and 11 via securing means such as any suitable bonding glue or a plurality of bolts 13 on which nuts 14 and washers 15 are positioned. The securing means, only two of which are shown, may also consist of pressure screws which extend through apertures in one of said end caps and into corresponding threaded apertures in the other end cap. The bolts 13 extend through apertures 16 and 17 in end caps 10 and 11.

The lower end cap or plate 10 is provided with a central opening having a small diameter section 18 and a threaded larger diameter section 19. End cap 10 is also provided on one surface thereof with a centrally located small countersunk section 20, a larger countersunk 21, and a groove 22. A tube 23, which extends through an opening 24 in a threaded coupling 25, is retained in the small diameter opening section 18 by coupling 25 which is threaded into the threaded opening section 19 of end cap 10. Tube 23 extends at one end through countersunk section 20 and a seal 26, such as an O-ring, is positioned in countersink section 20 around tube 23 to prevent leakage of the sample or eluant fluid components along the central opening in end cap or plate 10, with tube 23 being connected at the opposite end to a point of use. Tube 23 extends into a central opening in support member 12'. A seal 27, such as an O-ring, is located in groove 22 to prevent leakage between "wafer" or "plate" 12 and end cap 10. Other seal means may also be employed.

Upper end cap or plate 11 is provided on one surface with a centrally located inlet opening 28 on one surface thereof and on the opposite surface with a countersink section 29 and an optional groove 30. A fluid source (sample and/or eluant), not shown, is connected to opening 28 which extends into countersink section 29. The inlet opening comprises a small diameter section 31 and a larger threaded diameter section 32 into which a coupling, not shown, may be secured for connecting the inlet opening of end cap 11 with a fluid reservoir which may contain the sample fluid or the eluting fluid. A fluid distribution system is positioned in countersink section 29, described in detail below, and a seal 33, such as an O-ring, is located in groove 30 to prevent leakage between upper end cap 11 and "wafer" 12.

The fluid distribution system basically comprises a member composed of a porous member 34, such as a sintered or porous ceramic or glass, or filter paper or mesh material or screen material, a retainer member 35, and a filler member 36, with the screen or mesh 34 being held in abutment with the bottom surface of countersink section 29 by retainer member 35, which, in turn, abuts against "wafer" 12. Thus, porous member 34 is retained in a space between the end cap 11 and retaining member 35. Retainer member 35 has a flat longitudinal surface 37 adjacent said porous member 34 and is provided on the opposite side with a countersink section 38 constructed so as to define an outer protruding ring-like section or flange 39 having a peripheral surface 40. A filler member 36 is also located in countersink 21 of end cap 10 and is provided with an opening 41 through which tube 23 extends.

As seen in FIG. 2, the screen or mesh 34 has cross-section substantially the same as the cross-section of countersink section 29 such that the inlet sample and elution fluid is distributed by the screen or mesh 34 in a uniform pattern into a space or passageway 42 located between end cap 11 and the peripheral surface 40 of ring-like section 39 of retainer member 35. By this arrangement, the inlet fluid is uniformly distributed to the outer surface area of the "wafer" 12 of the separating medium. The screen or mesh 34 also serves to retain the retaining member 35 in a central position. However, small balls or shims, as described hereinafter in reference to FIG. 4, can be used, if desired, to maintain the width of space 41.

In operation, a sample fluid, followed by an elution fluid, is directed through openings 31–32 into countersink section 29 and screen or mesh 34, and passes radially outwardly along the screen or mesh 34, and flat surface 37 of retainer member 35, to the opening or passageway 42, and through opening or passageway 42 onto the outer surface area of separation medium "wafer" 12, and then passes radially inwardly through the "wafer" 12 by capillary action, where it is separated into the various components, to a central opening or collection port 42 located in "wafer" 12, after which the fluid components exit via tube 23 to a point of use. The non-permeable backing, or support for matrix layer 12' functions to prevent the fluid from dropping through the separation medium of "wafer" 12.

One of the advantages of the present fluid distribution system (components 34 and 35) of this invention, apart form the reduction in cost compared with the grooved type distribution systems of the copending applications and issued patents referred to earlier herein, is in providing for more uniform, smooth distribution of the inlet fluid due to the use of a fine mesh or screen surface.

By way of example, one or both of end caps 10 and 11 may be constructed of metal, such as aluminum, stainless steel, or tin and the like or of a plastic material such as polyacetate, polycarbonate, acrylic and the like, which is compatible with or unreactive with the fluids (including solvents) passing therethrough. In end cap 10, the opening 18 may have a diameter of about 0.050" to about 0.10", with countersink section 20 having a depth of about 0.050" and cross-section of about 0.250" and with countersink section 21 having a depth of about 0.25" and radius of about 0.17". In end cap 11, the opening 31 may have a diameter of about 0.05" to about 0.25", with countersink section 29 having a depth of about 0.33" and cross-section of about 4.40". The screen or mesh 34 may be fabricated from stainless steel, polyester, aluminum or any suitable material, with a mesh size of about 100 to about 250 mesh, and cross-section of about 4.4", and thickness of about 0.005 to about 0.010". The retainer member 35 may be constructed of stainless steel, aluminum, polycarbonate, polyacetate, acrylic and the like, with a total cross-section of about 5.25", and with countersink section 36 having a radius of approximately 4.10". The section 39 of retainer member 35 may have a cross-section of about 0.55". The opening or passageway 42 has a width of about 0.005 to about 0.10". The "wafer" or thin matrix of separation medium member 12 may, for example, have a diameter of about 4.5 to about 4.75", a thickness of about 0.010 to 0.100 mils (100–200 microns), and composed of any suitable separation medium known in the art, which includes but not limited to ion exchange resins, cellulosic materials, agarose materials, sepharose materials and the like, coated, deposited as a thin layer on a suitable support member, receptacle or substrate such as filter paper, thin glass, quartz or ceramic plate, and the like, used in the technology of thin layer chromatography. The choice of the separation medium of "wafer" 12 depends on the sample or fluid component material desired to be separated in the column, as known in the art. The support, matrix, substrate or backup layer or member 12' may be constructed of glass, quartz, ceramic, filter paper, polymer sheets or membranes and the like, with a thickness of about 0.050". The separation medium is coated or deposited thereon by methods known in the art.

As can be seen, the end caps or plates 10 and 11 can be readily disassembled to remove and replace the separation medium "wafer" 12. Alternatively, the end caps or plates 10 and 11 can be bonded or glued together or to "wafer" 12, thereby eliminating the cost of the securing means (bolts 17 and the like) and making the entire column disposable. When the end caps are glued or bonded to "wafer" 12, the seals 27 and 33 (and their associated grooves) can be eliminated, provided that the glue or bond produces a leak-proof connection therebetween, thus further reducing the production cost o the column.

Figure 3:
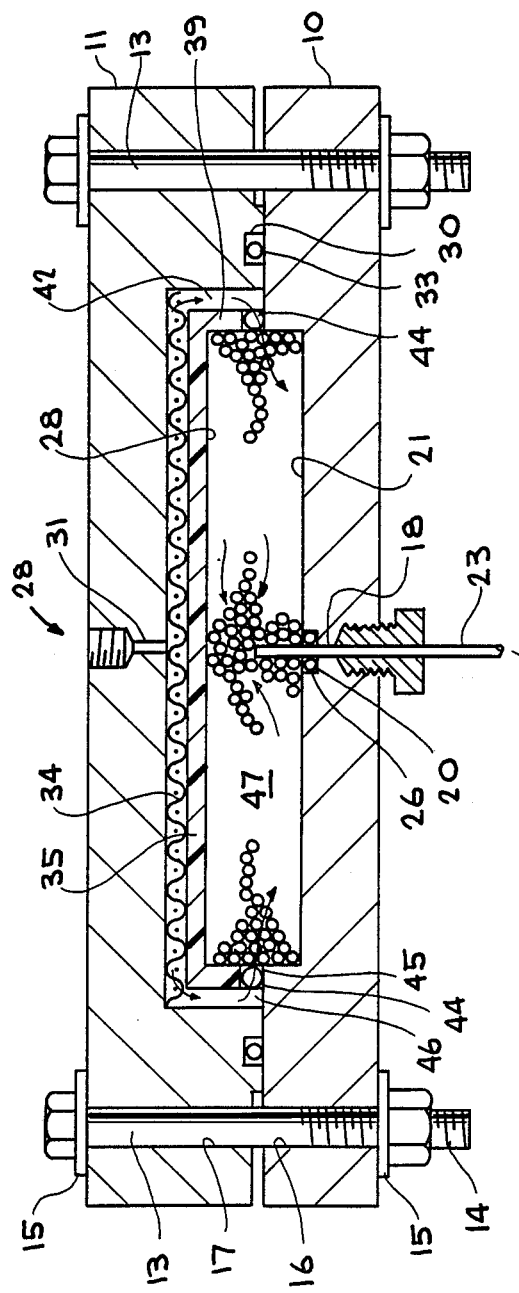
FIG. 3 is a cross-sectional view of an embodiment of the invention similar to the embodiment of FIG. 1 but which utilizes a bed of separation medium.

The embodiment of FIG. 3 is generally similar to the embodiment illustrated in FIG. 1 except that the "wafer" 12-12' of separation medium has been replaced by a packed bed of the appropriate separation medium of any known in the art. Additionally, the filler members 36 and 36' have been removed and the groove/seal assembly 22/27 has been eliminated. Corresponding structural components in FIG. 3 have been given similar reference numerals to those found in FIG. 1.

In view of the removal of the "wafer" 12-12', a plurality of spaced beads or balls 44 are positioned between the ring-like section 39 of retainer member 35 and a surface 45 of end cap or plate 10 to maintain a desired spacing 46 for passage of the fluid from space 42 into a bed 47 of separation medium. In this embodiment, four (4) spaced balls are utilized, only two being shown, which allow for substantially unimpeded fluid flow therearound. The balls 44 can be replaced by triangular shaped shims or other support members which function to retain the spacing 46.

The operation and assembly of the embodiment of FIG. 3 is essentially the same as that of the FIG. 1 embodiment, with the fluid flow therethrough being indicated by flow arrows. As in the FIG. 1 embodiment, the incoming fluid is distributed radially outward around a 360° path via mesh 34 and passes uniformly into the space or passage 42 for uniform distribution to the bed 47 of separation medium. The fluid passes horizontally inwardly through the medium for collection of the fluid components by a centrally located tube 23.

As in the FIG. 1 embodiment, the end caps 10 and 11 can be separated via retaining bolts 13 for replacement of the medium of bed 47, or the entire assembly can be made disposable as described above.

Figure 4:
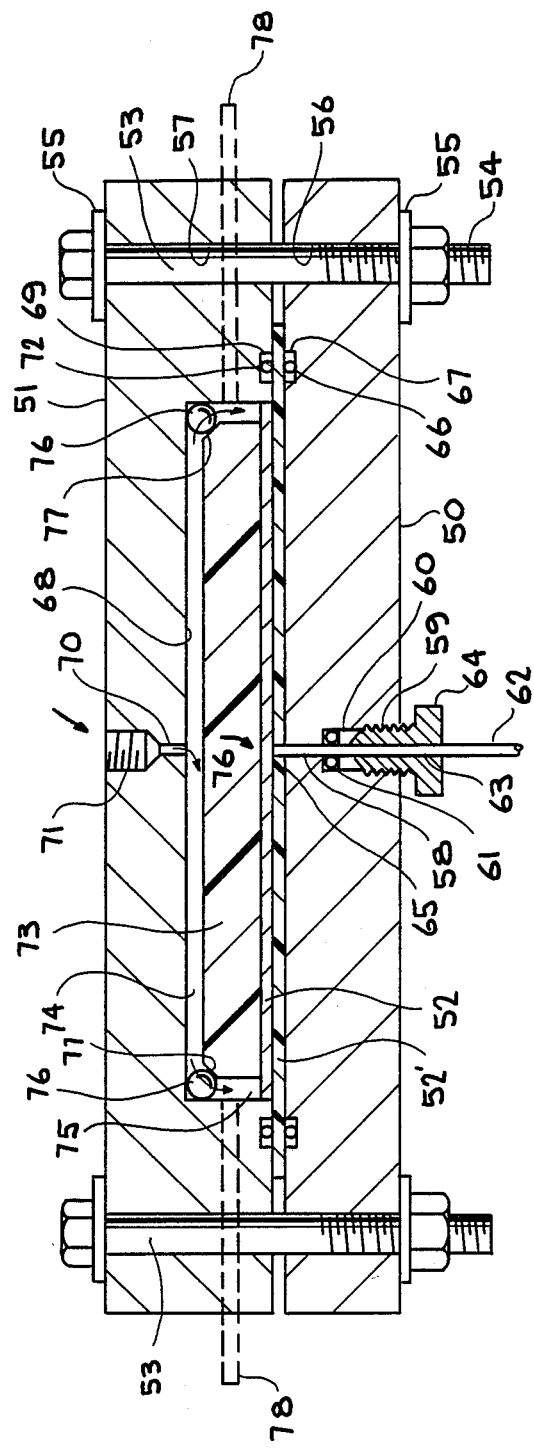
FIG. 4 is a cross-sectional view of an embodiment of the invention for high pressure applications.

The embodiment of FIG. 4 is particularly applicable or adaptable for use in component separation of fluids pumped at a relatively high pressure, in the range greater than about 200 psi, for example, while the embodiment of FIG. 1 is particularly suitable for low pressure applications. The difference between the two embodiments reside primarily in the fluid distribution and the retaining members of the "wafer" of the separation medium. As in the embodiment of FIG. 1, fluid passing through the separation medium does so by capillary action, with the medium being supported or backed by a non-permeable layer.

Basically, the embodiment of FIG. 4 comprises a housing formed by a lower section or end cap or plate 50 and an upper section or end cap or plate 51 between which is retained a "wafer" or a thin "plate" or "sheet" or layer or matrix of the separation medium 52, having a backing or support layer 52' if desired, via securing means, such as bolts 53 on which nuts 54 and washers 55 are positioned. The bolts 53 extend through apertures 56 and 57 in end caps 50 and 51. The illustrated securing means may be constructed differently, as described earlier in discussing the embodiment of FIG. 1.

The lower end cap or plate 50 is provided with a central opening having a small diameter section 58 and a threaded larger diameter section 59. At the inner end of opening section 59, end cap 50 is provided with a countersink 60 in which is located a seal 61, such as an O-ring. Similar to the embodiment of FIG. 1, a tube 62 extends through an opening 63 in a threaded coupling 64, mounted in threaded opening section 59, extends through countersink 60, seal 61, opening section 58, and an opening 65 in "wafer" support layer 12'. A seal 66, such as an O-ring, is located in groove 67 in end cap 50 to prevent leakage between "wafer" 52 and end cap 50.

Upper end cap or plate 51 is provided on an outer surface with a centrally located fluid inlet section generally indicated at or on the opposite or inner surface, with a countersink 68 and a groove 69. A fluid inlet opening, consisting of a small diameter section 70 and a threaded section 71, extends through inlet section of end cap 51. Eluting fluid from a source, not shown, is coupled into threaded section 71 of end cap 51. A fluid distribution arrangement, described below, is positioned in countersink section 68, and a seal 72, such as an O-ring, is located in groove 69 to prevent leakage between "wafer" 52 and end cap 51.

The fluid distribution system or arrangement basically comprises a member 73 positioned in countersink 68 and constructed to include a longitudinal surface and a peripheral surface so as to form space or passageways 74 and 75 between member 73 and adjacent surfaces of countersink 68. By way of example, space 74 has a thickness of about 0.01 to about 0.03", while the space 75 has a thickness also of about 0.01 to about 0.03". Thus, when fluid enters through opening section 70 into space 74, it immediately spreads radially outwardly over a 360° angle and flows into space 75, and then into and through separation medium "wafer" 52 in an inwardly and horizontal direction. The fluid components pass into a central opening or collection port 76 in the "wafer" 52, which is in fluid communication with tube 62, and are carried to a point of use or further analysis.

To maintain the desired spacing (passages 74 and 75) between end cap 51 and member 73, a plurality of spacer means, such as small balls 76, are located in grooves or cut-outs 77 in member 73. In this embodiment, four (4) balls 76 are used, with only two (2) being illustrated. The diameter of balls 76 is slightly larger than the thickness of spaces 74 and 75, with cut-outs 77 configured to conform with the shape and size of balls 76. Balls 76 may be replaced by other spacer means such as triangular shaped shims with cut-outs 77 configured to cooperate with the shape of the shims. Regardless of the configuration of the spacer means and cooperating cut-outs, the configuration, size, location and number are to be such as to cause minimal decrease in the flow patterns (360°) of fluid passing into the separation medium (wafer 12).

The inlet to the fluid distribution arrangement of FIG. 4 may also be through one or a plurality of radially extending passageways (only two shown), indicated at 78 by dotted lines, rather than through the inlet opening 71-70 at the center of end plate 51.

With the arrangement illustrated in FIG. 4, and with the fluid inlet being via inlet 71, the housing (end caps 50 and 51) and "wafer" 52 secured therein or deposited thereon, may be spun about a partial axis which provides for centrifugal fluid distribution through space 74, while not adversely affecting the passage of the fluid by capillary action radially inwardly through the "wafer" 52 of the separation medium.

While the countersink 21 in the lower end cap 10 of FIGS. 1 and 3 has been illustrated for simplicity of construction, if desired, it can be constructed so as to form a protruding central section of the end cap, such as illustrated in parent application Ser. No. 939,557 referenced earlier, whereby support for the "wafer" 12 is provided at the periphery and at the center thereof. With such a configuration of the countersink 21, the filler member 36' would need to be configured so as to cooperate with (extend around) the protruding central section of the end cap. Also, with this modified countersink configuration, the countersink 20 and seal 26 would be located at the inner end of the protruding central section of the end cap.

If desired, the retainer member may also be constructed to include a central projecting portion which would align with the protruding central section of end cap 10 as modified above, as also illustrated in patent application Ser. No. 939,557. Such a modification of retainer member 35 would require a modification of filter member 36 so as to cooperate with the central projecting portion of the retainer member.

While particular embodiments of the invention and specific materials and parameters have been illustrated and described to provide a better understanding of the invention, it is not intended to be exhaustive or to limit the invention to the particular illustrations or embodiments so described. The above embodiments were chosen and described in some detail in order to best explain the principles and the practical applications of the subject invention thereby to enable those skilled in the art to utilize and practice the invention in various other embodiments and modifications as are suitable for the particular use contemplated. Obviously many modifications and variations are possible in light of the above teaching. It is intended that the scope of the invention be defined by the claims appended hereto.

What is claimed is:

1. A chromatography column utilizing horizontal flow of sample material passing therethrough, comprising:
   a housing having a chamber therein and having a centrally located sample material inlet and a centrally located material component outlet,
   separation medium retained in said housing chamber, and fluid distribution means within said housing for directing sample material injected into a central section of said housing in a substantially uniform, radially outward direction from said central section to an outer section of said housing and onto an outer surface area of said separation medium, said fluid distribution means including a porous member, and a retainer member located intermediate said porous member and said separation medium except at an area adjacent said outer surface area of said separation medium, whereby sample material passes inwardly horizontally through said separation medium from said outer surface area, and material components discharging from said separation medium are directed into said centrally located material component outlet.

2. The column of claim 1, wherein said housing comprises a pair of end caps, and means for securing said end caps together, said fluid distribution means being located in one of said end caps.

3. The column of claim 2, wherein said separation medium is constructed as a thin matrix.

4. The column of claim 3, wherein said thin matrix of separation medium has an outer area peripherally secured between said end caps.

5. The column of claim 3, wherein said one of said pair of end caps is provided with a countersink section, said sample material inlet being in fluid communication with said countersink section, said fluid distribution means being positioned in said countersink section, and said material component outlet being located in another of said pair of caps.

6. The column of claim 5, wherein said porous member of said fluid distribution means is selected from the group consisting of screen material, mesh material and ceramic material.

7. The column of claim 6, wherein an outer periphery of said retainer member of said fluid distribution means is positioned in spaced apart relationship with a surface of said one of said pair of end caps which defines a side wall of said countersink section so as to define a passageway therebetween, and means for maintaining the spaced apart relationship.

8. The column of claim 7, wherein said means for maintaining the spaced apart relationship between said retainer member and said one of said pair of end caps comprises a plurality of spacer means selected from the group consisting of balls and shims.

9. The column of claim 7, wherein said retainer member includes a countersink section on one side thereof and an outer ring-like section, said ring-like section of said retainer member being in contact with said thin matrix of separation material.

10. The column of claim 9, wherein said thin matrix of separation material is constructed in the form of a wafer.

11. The column of claim 10, wherein said wafer is constructed to consist of a non-permeable support member and a layer of separation medium secured to said support member.

12. The column of claim 9, wherein said another of said pair of end caps includes a countersink section therein, said material component outlet being in fluid communication with said countersink section of said another end cap.

13. The column of claim 12, wherein said thin matrix of separation material includes a centrally located port into which sample material components pass, said port being in fluid communication with said material component outlet.

14. The column of claim 13, additionally including means connected to said material component outlet for directing sample material components entering said port in said thin matrix separation material from said housing to a point of use.

15. The column of claim 12, additionally including a filler member located in said countersink in each of said pair of end caps, and in contact with said thin matrix of separation medium.

16. The column of claim 1, wherein said separation medium consists of a packed bed of separation material retained in said chamber.

17. In a horizontal flow type chromatographic column having a housing containing a separation medium, and constructed to provide for horizontal flow of sample material through the separation medium, the improvement comprising:

a fluid distribution system for uniformly directing to said separation medium sample material entering said housing, said distribution system comprising, a porous member and a retaining member, said retaining member being located intermediate said porous member and said separation medium, said retaining member being constructed and located so as to uniformly direct sample material in a radially outward direction and prevent passage of sample material flowing onto said separation medium except at an outer peripheral surface area of said separation medium, whereby sample material is directed horizontally inward through said separation medium.

18. The improvement of claim 17, wherein said housing is constructed to include a countersink section in one end thereof, and wherein the fluid distribution system is located in said countersink section of said housing.

19. The improvement of claim 18, wherein said porous member is selected from the group consisting of screen material, mesh material and ceramic material.

20. The improvement of claim 18, wherein said porous member is in abutment with a bottom surface of said countersink section of said housing, and wherein said retainer member is in spaced apart relationship with a side surface of said countersink section of said housing so as to form a fluid passageway therebetween.

21. The improvement of claim 20, additionally including means for maintaining said retaining member in spaced apart relationship with said surface of said countersink section of said housing.

22. The improvement of claim 21, wherein said means comprises a plurality of spaced members selected from the group consisting of balls and shims.

23. The improvement of claim 18, wherein said porous member comprises a screen, and wherein said housing is provided with a sample material inlet at substantially a central location of said countersink section of said housing, such that sample material entering said countersink section passes radially outwardly along said screen to an outer area surface of said separation medium.

24. The improvement of claim 17, wherein said retaining member is constructed so as to contact said separation medium only at a peripheral portion thereof.

25. A chromatography column containing separation medium and utilizing horizontal flow of sample material therethrough, comprising:
- a housing forming a chamber therein, and having at least one inlet passage and a centrally located outlet passage, each connected at one end to said chamber,
- a thin wafer containing said separation medium and retained in said chamber of said housing so as to separate said inlet and outlet passages, and
- fluid distribution means within said chamber of said housing intermediate said inlet passage and said wafer for directing fluid in a substantially uniform manner about an outer periphery of said wafer said distribution means comprising a porous member and a retaining member, said retaining member being located intermediate said porous member and said separation medium,
- whereby fluid passes from said inlet passage horizontally through said separation medium, and into said outlet passage.

26. The column of claim 25, wherein said fluid distribution system includes a member positioned within said chamber and having a longitudinal surface thereof intermediate said inlet passage and said wafer, said member being constructed and positioned so as to define a first space between said longitudinal surface thereof and said housing and a second space between a peripheral surface thereof and said housing.

27. The column of claim 26, additionally including spacer means located between said member and said housing for maintaining said first and second spaces therebetween.

28. The column of claim 26, additionally including a porous member positioned in said first space.

29. The column of claim 26, wherein said member includes a longitudinal surface in abutment with said wafer except at a peripheral surface thereof.

30. The column of claim 25, wherein said thin wafer containing separation medium consists of a layer of a non-permeable support material and a layer of separation medium secured to said layer of support material.

31. The column of claim 25, wherein said housing consists of a pair of sections, and wherein said wafer of separation material is retained intermediate said pair of sections of said housing.

32. The column of claim 31, wherein said pair of housing sections are removably connected to one another.

* * * * *